US00PP30143P3

(12) United States Plant Patent
Bell

(10) Patent No.: US PP30,143 P3
(45) Date of Patent: Jan. 29, 2019

(54) BLUEBERRY PLANT NAMED 'RIDLEY 1212'

(50) Latin Name: ***Vaccinium* hybrid**
Varietal Denomination: Ridley 1212

(71) Applicant: Mountain Blue Orchards Pty Ltd., Lindendale, New South Wales (AU)

(72) Inventor: Ridley Bell, Lindendale (AU)

(73) Assignee: Mountain Blue Orchards Pty Ltd, Lindendale, New South Wales (AU)

( * ) Notice: Subject to any disclaimer, the term of this patent is extended or adjusted under 35 U.S.C. 154(b) by 0 days.

(21) Appl. No.: 15/731,835

(22) Filed: Aug. 10, 2017

(65) Prior Publication Data

US 2018/0049359 P1 Feb. 15, 2018

Related U.S. Application Data

(60) Provisional application No. 62/494,549, filed on Aug. 12, 2016.

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
CPC ... A01H 5/08; A01H 5/02; A01H 5/00; A01H 6/368
See application file for complete search history.

(56) References Cited

U.S. PATENT DOCUMENTS

| | | | | |
|---|---|---|---|---|
| PP20,695 | P2 * | 2/2010 | Wright | Plt./157 |
| PP23,684 | P3 | 6/2013 | Wright et al. | |
| PP26,972 | P3 * | 7/2016 | Bell | A01H 5/08 Plt./157 |

* cited by examiner

*Primary Examiner* — June Hwu
(74) *Attorney, Agent, or Firm* — Hahn Loeser & Parks, LLP

(57) ABSTRACT

The new blueberry plant variety 'Ridley 1212' is provided. 'Ridley 1212' is a commercial variety intended for use as fresh fruit for shipping, customer pick and processing markets and as a home garden plant. The variety is produced from a cross of seed parent 'M07-18-03' (unpatented) and pollen parent 'M05-05-04' (unpatented), which can be distinguished by its outstanding features.

8 Drawing Sheets

Latin name of the genus and species:
Genus—*Vaccinium.*
Species—hybrid.
Variety denomination: The new blueberry plant claimed is of the variety denominated 'RIDLEY 1212'.

STATEMENT REGARDING FEDERALLY-SPONSORED RESEARCH AND DEVELOPMENT

None.

BACKGROUND OF THE INVENTION

The present invention relates to a new and distinct perennial variety of *Vaccinium* hybrid (Southern Highbush Blueberry), which has been given the variety denomination of 'Ridley 1212'. Its market class is that of a fruiting plant. 'Ridley 1212' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2009 from the controlled pollination of seed parent 'M07-18-03' (unpatented) with pollen parent 'M05-05-04' (unpatented). The new cultivar was discovered and selected as a single plant within a population of 100 resulting *Vaccinium* hybrid plants from this controlled pollination in 2012 in a commercial field plantation environment at Lindendale, New South Wales, Australia. Selection criteria was a combination of strong plant growth vigor and open bush, upright to semi-upright plant growth habit, low chilling requirement, early to medium time of flowering and fruit ripening, medium to large, sweet, firm, crisp fruit suited to handling, ripe berries able to shake off leaving unripe fruit on the bush making machine harvesting possible, desirable tasting berries and small picking scar.

The selection was subsequently evaluated for a number of years at the commercial farms at Lindendale, New South Wales, Australia.

SUMMARY OF THE INVENTION

The new *Vaccinium* hybrid cultivar is a selection resulting from seedlings produced in a breeding program of *Vaccinium* at Lindendale, NSW, Australia in 2009 from the controlled pollination of seed parent 'M07-18-03' (unpatented) with pollen parent 'M05-05-04' (unpatented). The seed parent was produced from a cross between 'S01-28-01' and 'S01-23-01'. The pollen parent was produced from a cross between 'C95-12' (U.S. Plant Pat. No. 23,684) and 'C96-67' (unpatented).

The new blueberry variety was designated M12-12-12, and has been planted in replicated trials since 2013.

The new *Vaccinium* hybrid cultivar is a selection resulting from seedlings produced in a controlled breeding program of *Vaccinium* at Lindendale, NSW, in 2012 from the controlled pollination of seed parent M07-18-03 (unpatented) and pollen parent M05-05-04 (unpatented).

Asexual reproduction of the new cultivar by softwood cutting propagation since 2012 at Lindendale, New South Wales has demonstrated that the new cultivar reproduces true to type with all of the characteristics, as herein described, firmly fixed and retained through successive generations of such asexual propagation.

The new *Vaccinium* hybrid cultivar is a selection resulting from seedlings produced in a breeding program of *Vaccinium* at Lindendale, NSW, Australia in 2009 from the controlled pollination of seed parent 'M07-18-03' (unpatented) with pollen parent 'M05-05-04' (unpatented). The new cultivar was discovered and selected as a single plant within a population of 100 resulting *Vaccinium* hybrid plants from this controlled pollination in 2012 in a commercial field plantation environment at Lindendale, New South Wales, Australia. Selection criteria was a combination of strong plant growth vigor and open bush, upright to semi-upright plant growth habit, low chilling requirement, early to medium time of flowering and fruit ripening, medium to large, sweet, firm, crisp fruit suited to handling, ripe berries able to shake off leaving unripe fruit on the bush making machine harvesting possible, desirable tasting berries and small picking scar.

The selection was subsequently evaluated for a number of years at the commercial farms at Lindendale, New South Wales, Australia and farms at Tabulam, New South Wales, Australia.

The following characteristics of the new cultivar have been repeatedly observed and can be used to distinguish M12-12-12 (Ridley 1212) as a new and distinct cultivar of *Vaccinium* hybrid plant:

1. Upright to semi-upright and open bush,
2. Early to mid timing of flowering beginning
3. Early to mid timing of fruit ripening.
4. Dark blue berry color with good bloom.
5. Very firm and crisp berry.
6. Dry picking scar.
7. Medium to large berry size.
8. Berry sweetness is very high.

Plants of the new cultivar differ from plants of the seed parent 'M07-18-03' primarily in strong plant growth vigor, rounder fruit shape, firm fruit firmness, high level of sweetness and medium sized leaves whereas the seed parent has very strong plant growth vigor, more oblate fruit shape, medium fruit firmness, medium level of sweetness and large sized leaves. Plants of the new cultivar differ from plants of the pollen parent 'M05-05-04' primarily in upright to semi-upright plant growth habit, medium to large fruit size, and highly rated fruit flavor whereas the pollen parent has a more upright plant growth habit, medium fruit size, and lower rated fruit flavor.

BRIEF DESCRIPTION OF THE DRAWINGS

The accompanying photographic illustration shows typical specimens in full color of the foliage and fruit of the new variety 'Ridley 1212'. The colors are as nearly true as is reasonably possible in a color representation of this type. All photographs relate to plants of approximately 2 years of age.

Figure 1:
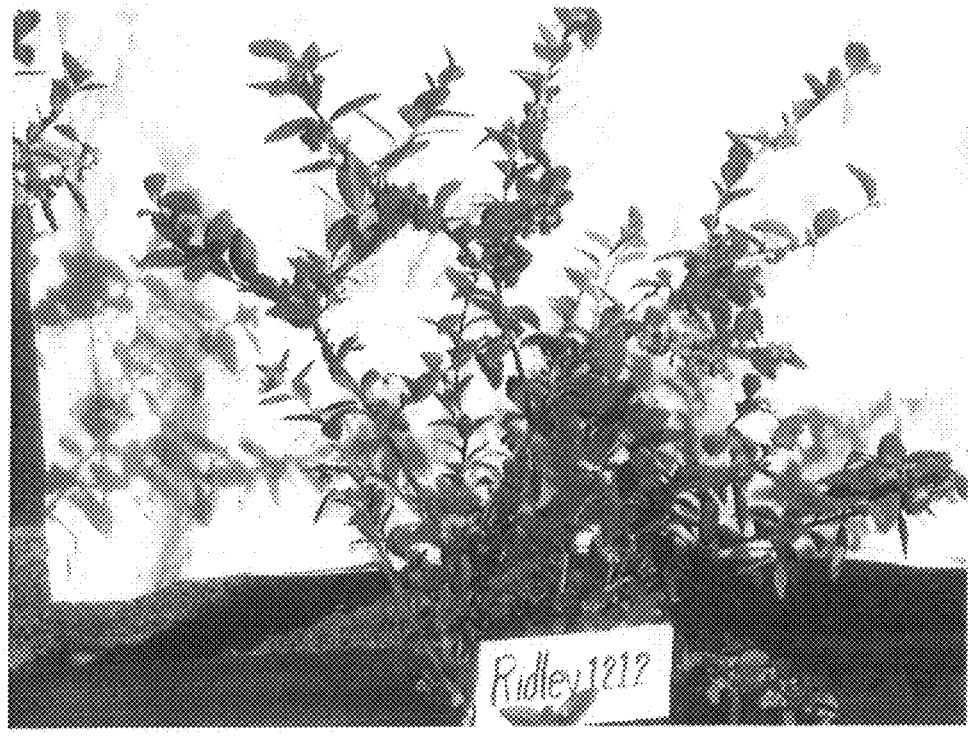
FIG. 1 is a photograph of the new variety 'Ridley 1212', demonstrating the plant's open and upright growth habit.
Figure 2:
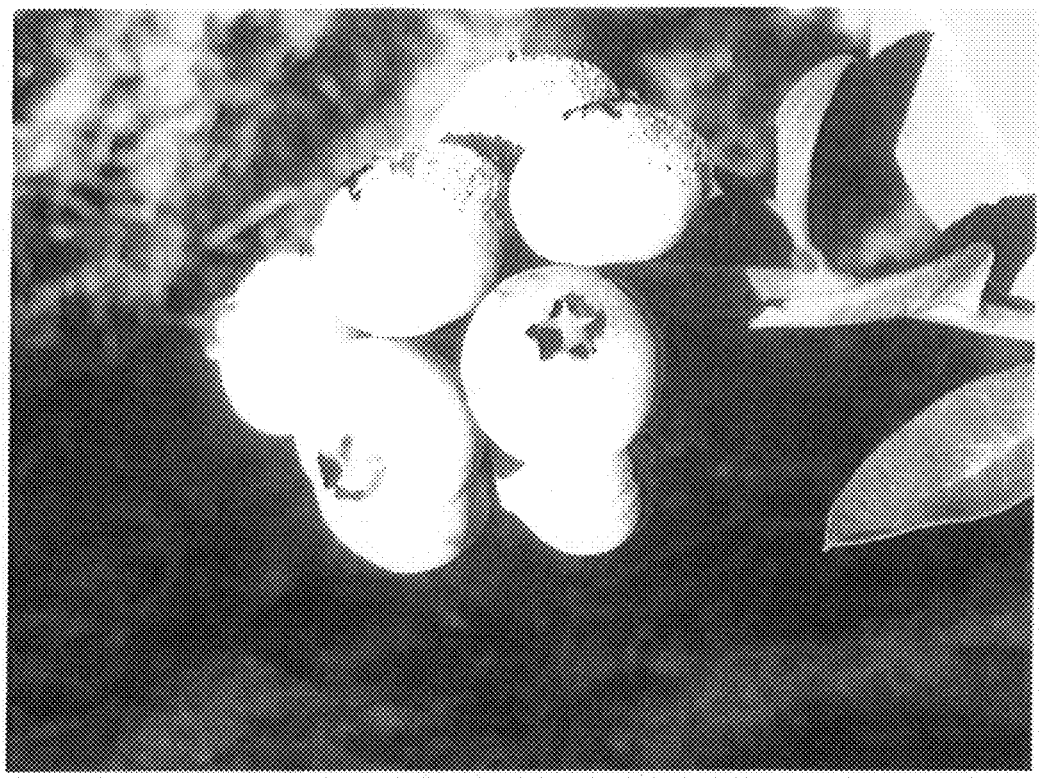
FIG. 2 is a photograph of the fruit of the new variety 'Ridley 1212'.
Figure 3:
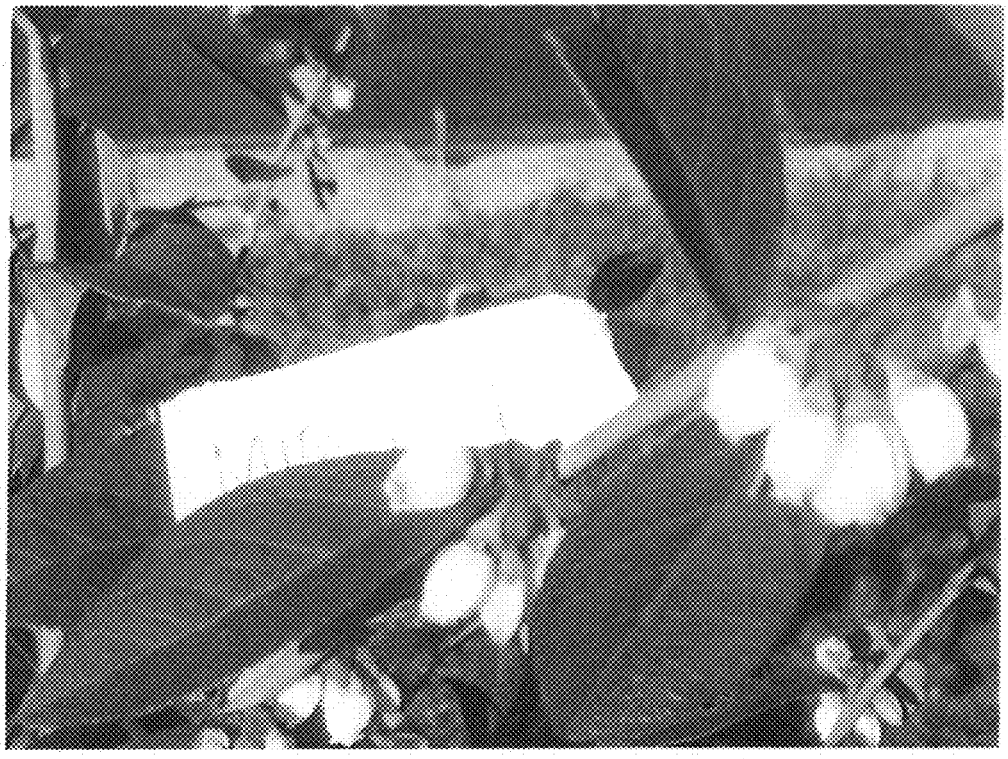
FIG. 3 is a photograph of the flowers of the new variety 'Ridley 1212'.
Figure 4:
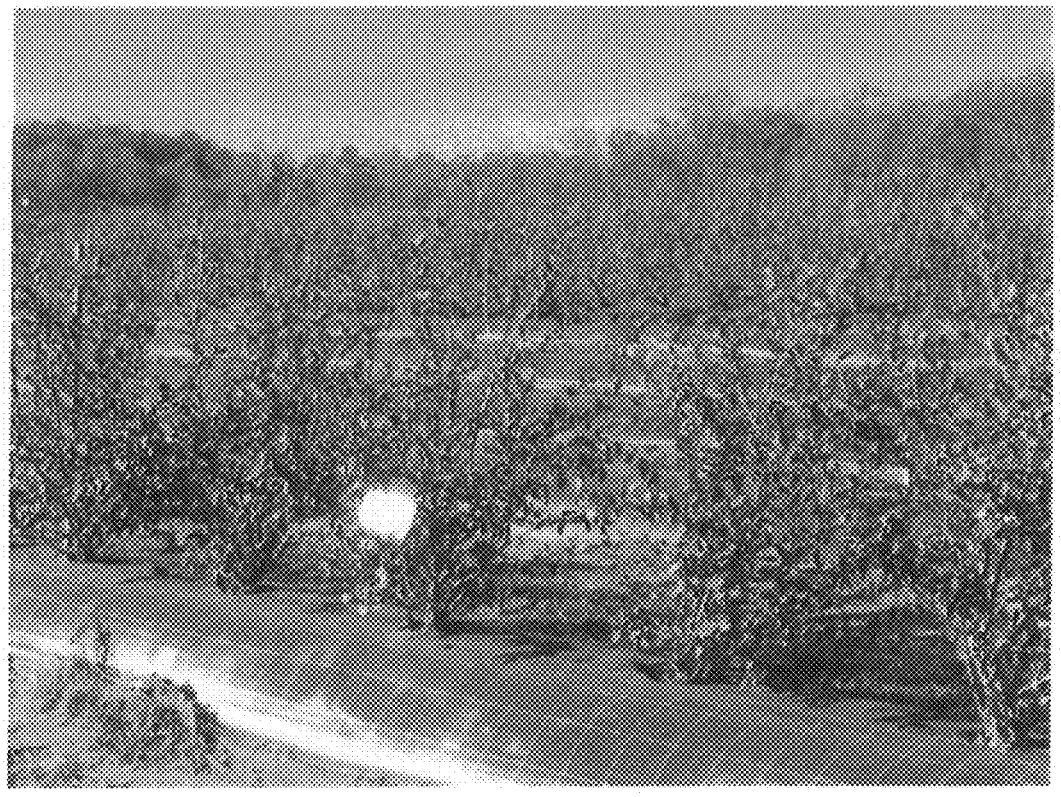
FIG. 4 is a photograph of the fall foliage of the new variety 'Ridley 1212'.
Figure 5:
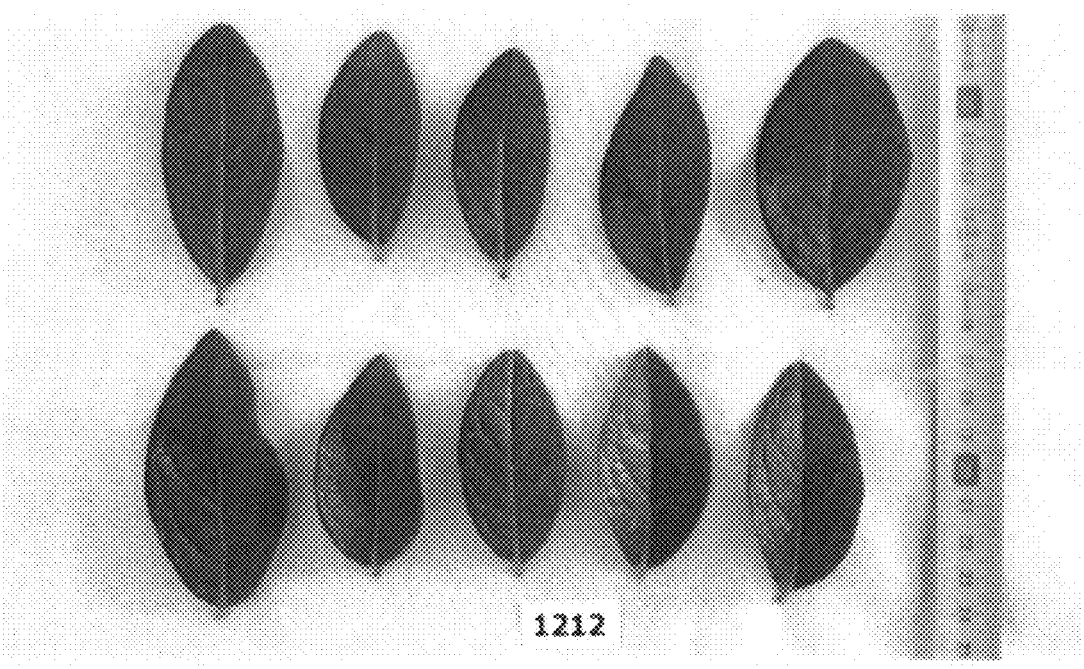
FIG. 5 is a photograph of the leaves of the new variety 'Ridley 1212'.
Figure 6:
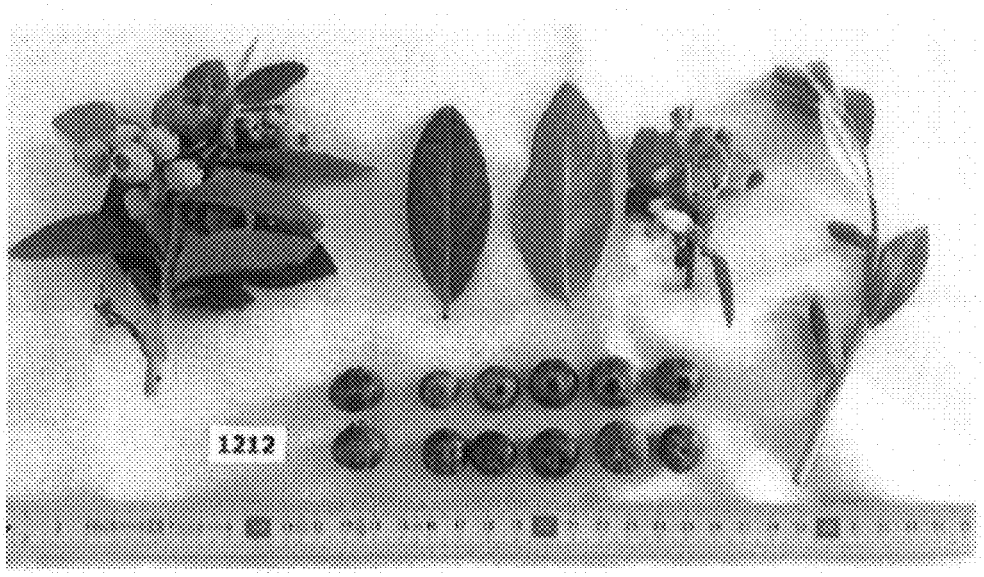
FIG. 6 is a photograph of the leaves, fruit, new shoot, inflorescence and fruit cluster of the new variety 'Ridley 1212'.
Figure 7:
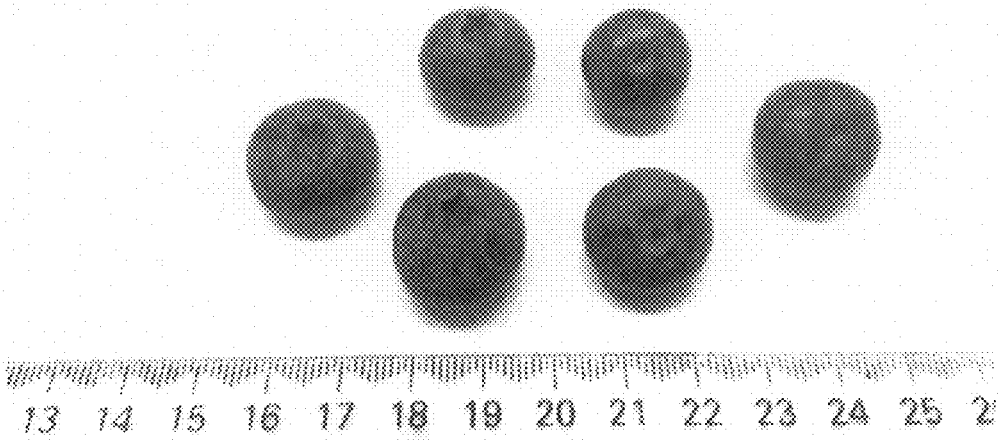
FIG. 7 is a photograph of fruit of the variety 'Ridley 1212'.
Figure 8:
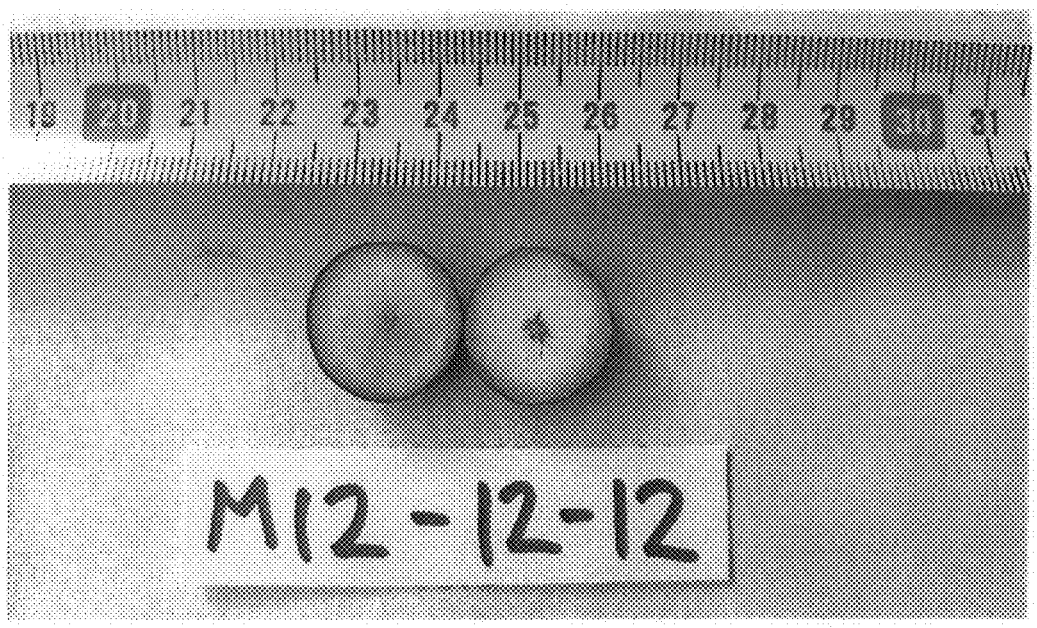
FIG. 8 is a photograph of fruit cross section of the variety 'Ridley 1212'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley 1212'. The data which defines these characteristics was collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia.

Color notations are based on *The Royal Horticultural Society Colour Chart*, of The Royal Horticultural Society, London, 2015 edition.

Classification:

*a. Family.*—Ericaceae.
*b. Genus.*—*Vaccinium.*
*c. Species.*—hybrid.
*d. Common name.*—Southern Highbush Blueberry.

Parentage:

*Female parent.*—'M07-18-03' (unpatented).
*Male parent.*—'M05-05-04.' (unpatented).

Market class: A fruiting plant intended for use as fresh fruit for shipping, hand pick, customer pick, machine harvest and processing markets and as a home garden plant.

PLANT

General:

*Parentage.*—Female Parent — 'M07-18-03' (unpatented). Male Parent — 'M05-05-04' (unpatented).
*Plant height.*—1.8 m.
*Plant width.*—1.2 m.
*Growth habit.*—Upright to semi-upright.
*Growth.*—Strong vigor.
*Productivity.*—Greater than 5 kg per season from 3-4 year old plants planted at 3.0 m×0.9 m density.
*Fruiting type.*—On one year old shoots only.
*Cold hardiness.*—Not tested.
*Cold tolerance.*—Not tested.

*Chilling requirement*.—Has not been grown in all environments and is typically grown as an evergreen crop where chilling hours are not important. 'Ridley 1212' is classed as 'low chill', typical of Southern Highbush Blueberry varieties with an estimated chilling requirement of 250 hours (not tested).
*Tolerance to disease*.—Moderate resistance to root disease (Phytophthora spp.) and good resistance to blueberry rust.
*Leafing*.—Vegetative bud burst is late when grown as an evergreen in Australia.
*Twigginess*.—Low.

STEM

General:
*Suckering tendency*.—Plants typically have 5-7 major canes per plant from a base 30 cm in diameter on 6 year old plants.
*Mature cane color*.—Color greyed green 198C.
*Mature cane length*.—0.8-0.9 m.
*Mature cane width*.—1.2 cm.
*Bark texture*.—Medium roughness (typical of species.
*Surface texture of new wood*.—Smooth.
*Internode length on strong, new shoots*.—15-20 mm.
*Fruiting wood*.—To 15 cm in length.

FOLIAGE

General:
*Time of beginning of leaf bud burst*.—Late (October in Tabulam, NSW, Australia).
*Leaf color* (*top side*).—Yellow green 147A.
*Leaf color* (*under side*).—Yellow green 147C.
*Leaf arrangement*.—Alternate.
*Leaf shape*.—Elliptic.
*Leaf margins*.—Entire.
*Undulation of margin*.—Weak.
*Leaf venation*.—Reticulate.
*Leaf apices*.—Acuminate.
*Leaf bases*.—Obtuse.
*Leaf length*.—60-70 mm.
*Leaf width*.—30-34 mm.
*Leaf length/width ratio*.—Medium.
*Leaf nectaries*.—Absent.
*Pubescence of upper side*.—Absent.
*Pubescence of lower side*.—Absent.
*Cross sectional profile*.—Flat.
*Longitudinal profile*.—Straight.
*Attitude*.—Semi-upright to horizontal.
Petioles:
*Length*.—1.0 to 3.0 mm.
*Width*.—2.0 mm.
*Color*.—Yellow green 146C-147C.

FLOWERS

General:
*Time of beginning of flowering*.—Early to medium (mid May to early July at Lindendale, NSW Australia).
*Time of* 50% *anthesis*.—Mid June at Lindendale, NSW Australia.
*Flower shape*.—Urceolate.
*Flower bud density*.—Medium density.
*Flower fragrance*.—Weak.
Corolla:
*Color*.—White NN155D.
*Length*.—10-13 mm.
*Width*.—6-9 mm.
*Aperture width*.—3-5 mm.
*Anthocyanin coloration of corolla*.—Absent, occasional in bud stage.
*Corolla ridges*.—Present.
*Protrusion of stigma*.—Usually absent.
Inflorescence:
*Length*.—40 to 70 mm.
*Diameter*.—20-30 mm.
*Length of peduncle*.—15 mm.
*Surface texture of peduncle*.—Smooth.
*Color of peduncle*.—146C.
*Length of pedicel*.—7-10 mm.
*Surface texture of pedicel*.—Smooth.
*Color of pedicel*.—147C.
*Number of flowers per cluster*.—9-14.
*Flower cluster density*.—Medium.
Calyx (with sepals):
*Diameter*.—9-11 mm.
*Color* (*sepals*).—Green 138C.
Stamen:
*Length*.—4-5 mm.
*Number per flower*.—Approximately 10.
*Filament color*.—Yellow green 144D.
Pistil:
*Length*.—10-13 mm.
*Style: Length*.—5-6 mm.
*Ovary color* (*exterior*).—Yellow green 147C proximally and changing to Yellow green 144D distally (towards sepals).
Anther:
*Length*.—3.0-3.5 mm.
*Number*.—Approximately 10.
*Color*.—Grayed orange 167C-D.
Pollen:
*Abundance*.—Medium.
*Color*.—Grayed orange 167C-D.
*Self-compatibility*.—75% fruit set with own pollen in tests at Lindendale, NSW Australia.

FRUIT

General:
*Time of fruit ripening*.—Early to medium (mid August to mid October at Lindendale, NSW Australia).
*Time of* 50% *maturity*.—Mid-late September.
*Fruit development period*.—65 days.
*Cluster density*.—Medium, 6-9 berries per cluster.
*Unripe fruit color*.—Green 138A.
*Ripe berry color when bloom is removed*.—Black 202A.
*Berry surface wax abundance*.—Strong.
*Berry flesh color*.—Grayed green 194C, lightening to 194D, then 193D.
*Berry weight*.—3.0-3.5 g.
*Berry height from calyx to scar*.—12-14 mm.
*Berry diameter*.—21 mm.
*Berry shape*.—Oblate.
*Fruit stem scar*.—Small (dry).
*Sweetness when ripe*.—Very high.
*Firmness when ripe*.—Firm.
*Acidity when ripe*.—Medium.

*Storage quality*.—Good, lasted 10 weeks at 2 degrees Celsius in tests. Not tested with modified atmosphere storage yet.

*Suitability for mechanical harvesting*.—Upright plant habit and very firm fruit firmness, strong blush and fruit shape suited to mechanical harvesting. Shake requirement and season compactness not yet tested.

*Self-fruitfulness*.—75% fruit set with own pollen in tests at Lindendale, NSW Australia.

*Uses*.—Fresh fruit for shipping, customer pick and processing markets and as a home garden plant.

SEED

General:

*Seed abundance in fruit*.—Abundant.

*Seed color*.—Greyed orange 164A.

*Seed length*.—1.5-2.0 mm.

TABLE 1

COMPARISON BETWEEN COMMERCIAL CULTIVARS

| Organ | Context | Ridley 1212 |
|---|---|---|
| Plant | vigour | strong |
| Plant | growth habit | upright to semi-upright |
| One-year-old shoot | color | green |
| One-year-old shoot | length of internode | medium |
| Leaf | length | long |
| Leaf | width | medium |
| Leaf | shape | elliptic |
| Leaf | color of upper side | green |
| Leaf | intensity of green color on upper side | medium |
| Leaf | margin | entire |
| Flower bud | anthocyanin coloration | weak |
| Flower | shape of corolla | urccolate |
| Flower | size of corolla tube | medium |
| Flower | anthocyanin coloration of corolla tube | absent or very weak |
| Flower | ridges on corolla tube | present |
| Fruit cluster | density | medium |
| Unripe fruit | intensity of green color | light |
| Fruit | size | large |
| Fruit | shape in longitudinal section | oblate |
| Fruit | attitude of sepals | erect |
| Fruit | diameter of calyx basin | medium |
| Fruit | depth of calyx basin | deep |
| Fruit | intensiy of bloom | strong |
| Fruit | color of skin | dark blue |
| Fruit | firmness | firm |
| Fruit | sweetness | very high |
| Fruit | acidity | medium |
| Time of | vegetative bud burst | Late (October) |
| Time of | beginning of flowering | early to medium |
| Time of | beginning of fruit ripening | early to medium |

TABLE 1-continued

COMPARISON BETWEEN COMMERCIAL CULTIVARS

| Organ | Ridley 3402 U.S. Plant Pat. No. 26,972 | Ridley 0501 | C99-42 U.S. Plant Pat. No. 20,695 |
|---|---|---|---|
| Plant | strong | medium | medium to strong |
| Plant | semi-upright | upright to semi-upright | semi-upright |
| One-year-old shoot | green | green | green |
| One-year-old shoot | medium | medium | medium |
| Leaf | medium to long | long | long to very long |
| Leaf | medium to broad | medium to broad | medium to broad |
| Leaf | elliptic | elliptic | elliptic |
| Leaf | green | green | green |
| Leaf | medium | light to medium | medium |
| Leaf | entire | entire | entire |
| Flower bud | weak | weak | weak |
| Flower | urccolate | urccolate | urccolate |
| Flower | small to medium | medium | medium |
| Flower | absent or very weak | absent or very weak | weak to medium |
| Flower | present | present | present |
| Fruit cluster | medium | medium to dense | dense |
| Unripe fruit | light | light | light |
| Fruit | medium | medium | large |
| Fruit | oblate | round | round |
| Fruit | erect | erect | erect |
| Fruit | medium | medium to large | medium |
| Fruit | medium to deep | deep | deep to very deep |
| Fruit | strong | weak to medium | medium |
| Fruit | dark blue | dark blue | dark blue |
| Fruit | soft to medium | medium to firm | medium |
| Fruit | medium to high | low to medium | medium |
| Fruit | medium to high | medium to high | low to medium |
| Time of | Medium (September) | Medium (September) | Early (August) |
| Time of | early | very early | early to medium |
| Time if | early to medium | early to medium | early to medium |

The invention claimed is:

1. A new and distinct variety of blueberry plant named 'Ridley 1212', substantially as illustrated and described herein.

* * * * *